United States Patent
Kocur et al.

(10) Patent No.: US 7,637,940 B2
(45) Date of Patent: Dec. 29, 2009

(54) STENT WITH BIOABSORBABLE MEMBRANE

(75) Inventors: Gordon J. Kocur, Lino Lakes, MN (US); John Blix, Maple Grove, MN (US); Thomas E. Broome, Prior Lake, MN (US); Adam Jennings, Buffalo, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 234 days.

(21) Appl. No.: 11/774,202

(22) Filed: Jul. 6, 2007

(65) Prior Publication Data

US 2009/0012596 A1 Jan. 8, 2009

(51) Int. Cl.
*A61F 2/06* (2006.01)
(52) U.S. Cl. ..................... 623/1.35; 623/1.38
(58) Field of Classification Search ........ 623/1.11–1.42
See application file for complete search history.

(56) References Cited

U.S. PATENT DOCUMENTS

| | | | |
|---|---|---|---|
| 5,358,475 A | 10/1994 | Mares et al. | |
| 5,772,439 A | 6/1998 | Yakaoka et al. | |
| 6,169,046 B1 | 1/2001 | Shikata et al. | |
| 6,391,033 B2 * | 5/2002 | Ryan | 606/108 |
| 6,685,956 B2 | 2/2004 | Chu et al. | |
| 6,689,374 B2 | 2/2004 | Chu et al. | |
| 6,783,543 B2 | 8/2004 | Jang | |
| 7,070,616 B2 | 7/2006 | Majercak et al. | |
| 7,135,039 B2 | 11/2006 | De Scheerder et al. | |
| 7,172,765 B2 | 2/2007 | Chu et al. | |
| 7,270,675 B2 | 9/2007 | Chun et al. | |
| 7,347,869 B2 | 3/2008 | Hojeibane et al. | |
| 7,351,256 B2 | 4/2008 | Hojeibane et al. | |
| 7,387,639 B2 * | 6/2008 | Bourang et al. | 623/1.11 |
| 7,481,834 B2 * | 1/2009 | Kaplan et al. | 623/1.15 |
| 2001/0044650 A1 | 11/2001 | Simso et al. | |
| 2003/0074049 A1 * | 4/2003 | Hoganson et al. | 623/1.13 |
| 2003/0181923 A1 | 9/2003 | Vardi | |
| 2003/0225447 A1 | 12/2003 | Majercak et al. | |
| 2003/0236568 A1 | 12/2003 | Hojeibane et al. | |
| 2004/0019374 A1 | 1/2004 | Hojeibane et al. | |
| 2004/0034408 A1 | 2/2004 | Majercak et al. | |
| 2004/0059406 A1 | 3/2004 | Cully et al. | |
| 2004/0093069 A1 * | 5/2004 | Priewe et al. | 623/1.15 |
| 2004/0172121 A1 | 9/2004 | Eidenschink et al. | |
| 2005/0043585 A1 | 2/2005 | Datta et al. | |
| 2005/0043816 A1 | 2/2005 | Datta et al. | |
| 2005/0102023 A1 * | 5/2005 | Yadin et al. | 623/1.15 |
| 2005/0267570 A1 * | 12/2005 | Shadduck | 623/1.44 |

(Continued)

FOREIGN PATENT DOCUMENTS

DE 10223399 12/2003

(Continued)

*Primary Examiner*—Suzette J Gherbi
(74) *Attorney, Agent, or Firm*—Vidas, Arrett & Steinkraus P.A.

(57) ABSTRACT

In at least one embodiment, the invention is directed to a stent having a tubular wall where at least a portion of the tubular wall comprises a bioabsorbable membrane. In the portion of the tubular wall containing the bioabsorbable membrane, the members (e.g. struts and connectors) of the stent are embedded in the bioabsorbable membrane. In at least one embodiment, the stent is also configured to elute a therapeutic agent.

9 Claims, 14 Drawing Sheets

U.S. PATENT DOCUMENTS

| | | |
|---|---|---|
| 2006/0136042 A1 | 6/2006 | Holman et al. |
| 2006/0155366 A1* | 7/2006 | LaDuca et al. .............. 623/1.23 |
| 2007/0112418 A1 | 5/2007 | Eidenschink et al. |
| 2007/0135904 A1 | 6/2007 | Eidenschink et al. |
| 2007/0208419 A1 | 9/2007 | Meyer et al. |
| 2007/0276464 A1 | 11/2007 | Valencia et al. |
| 2008/0036113 A1 | 2/2008 | Chun et al. |
| 2008/0046066 A1 | 2/2008 | Jenson et al. |
| 2008/0086191 A1* | 4/2008 | Valencia et al. ............ 623/1.11 |
| 2008/0288041 A1* | 11/2008 | Holman et al. ............. 623/1.11 |
| 2009/0005848 A1* | 1/2009 | Strauss et al. ................ 623/1.2 |
| 2009/0012605 A1* | 1/2009 | Zago et al. ................. 623/1.42 |

FOREIGN PATENT DOCUMENTS

| | | |
|---|---|---|
| WO | 02/24247 | 3/2002 |
| WO | 2005/034809 | 4/2005 |
| WO | 2006/028925 | 3/2006 |
| WO | 2006/044637 | 4/2006 |
| WO | 2007/055768 | 5/2007 |

* cited by examiner ced stent of FIG. 6 with at least one bioabsorbable membrane engaging the side branch to the perimeter member.
STENT WITH BIOABSORBABLE MEMBRANE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent having a tubular wall where at least a portion of the tubular wall comprises a bioabsorbable membrane. In the portion of the tubular wall containing the bioabsorbable membrane, the members (e.g. struts and connectors) of the stent are embedded in the bioabsorbable membrane.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 1a-c illustrate a strut embedded in a bioabsorbable membrane.

DETAILED DESCRIPTION OF THE INVENTION

Figure 1A:
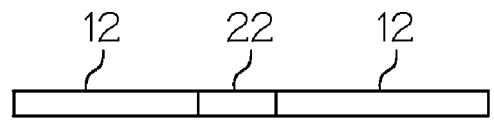

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The invention is directed to stent embodiments where a bioabsorbable membrane 12 forms at least a portion of the tubular wall of the stent 10. The tubular wall of the stent 10 comprises members, e.g. struts and connectors. In at least one embodiment, at least a portion of members forming the tubular wall is embedded in a bioabsorbable membrane 12. In at least one embodiment, the bioabsorbable membrane 12 is capable of a high percentage of elongation so that when the stent 10 is expanded, the bioabsorbable membrane 12 also expands. Note that the bioabsorbable membrane 12 can be constructed as, for example, but not limited to, a mesh, weave, or as a braid. Thus, in at least one embodiment, the bioabsorbable membrane 12 is made of a fabric-like material.

Figure 1B:
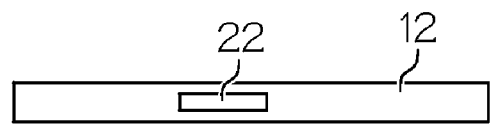
Figure 1C:
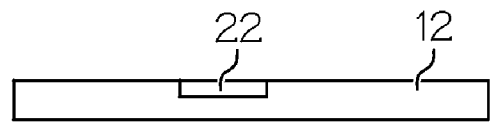

FIGS. 1a-c are cross-sections of a tubular wall of a stent where a portion of the stent 10, in these examples, a strut 22, is embedded in a bioabsorbable membrane 12. In FIG. 1a, the strut 22 and the bioabsorable membrane 12 have the same thickness so that the tubular wall of the stent 10 has a uniform thickness in that region. In this embodiment, only two sides of the strut 22 are engaged to the bioabsorbable membrane 12. In FIG. 1b, all of the sides of the strut 22 are engaged to the bioabsorbable membrane 12. Thus, in this embodiment, the thickness of the tubular wall of the stent 10 in that region depends upon the thickness of the bioabsorbable membrane 12. In addition, the thickness of the bioabsorbable membrane 12 in FIG. 1b is greater thickness than the thickness of the strut 22. Although all sides of the strut 22 in FIG. 1b is surrounded by the bioabsorbable membrane 12, it is within the scope of the invention for the bioabsorable membrane 12 to surround only three sides of the strut 22, as shown in FIG. 1c.

As used in this application, bioabsorbable also means biodegradable, degradable, biologically degradable, erodable, bioresorbable, and the like. The material used to make the bioabsorbable membrane 12 dissolves, dissociates, or otherwise breaks down in the body without ill effect. In some embodiments, the bioabsorable membrane 12 is made from porous material. In other embodiments, the bioabsorbable membrane 12 is made from non-porous material. In at least one embodiment, the material forming the bioabsorbable membrane 12 is woven. In at least one embodiment, the material forming the bioabsorbable membrane 12 is braided.

Examples of materials suitable for the bioabsorbable membrane 12 include, but are not limited to, poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen, hyaluronic acid, etc., and mixtures thereof.

As used herein, the term "polylactide" is equivalent to "poly (lactic acid)" as meaning a polymer of lactic acid. In particular, DL-lactide is a lactide derived from a roughly racemic mixture of lactic acid, and this nomenclature is interchangeable with (DL) lactic acid. Similarly, the terms polyglycolide and poly (glycolic acid) are equivalent.

Other suitable materials that can be used for the bioabsorbable membrane 12 can be found in U.S. Pat. No. 5,358,475, entitled High Molecular Weight Bioresorbable Polymers and Implantable Devices Thereof, U.S. Pat. No. 7,070,616, entitled Implantable Valvular Prosthesis, and U.S. Patent Application Publication No. 2005/0043816, entitled Reticulated Elastomeric Matrices, Their Manufacture and Use in Implantable Devices, each of which are incorporated by reference herein in their entirety.

Figure 2:
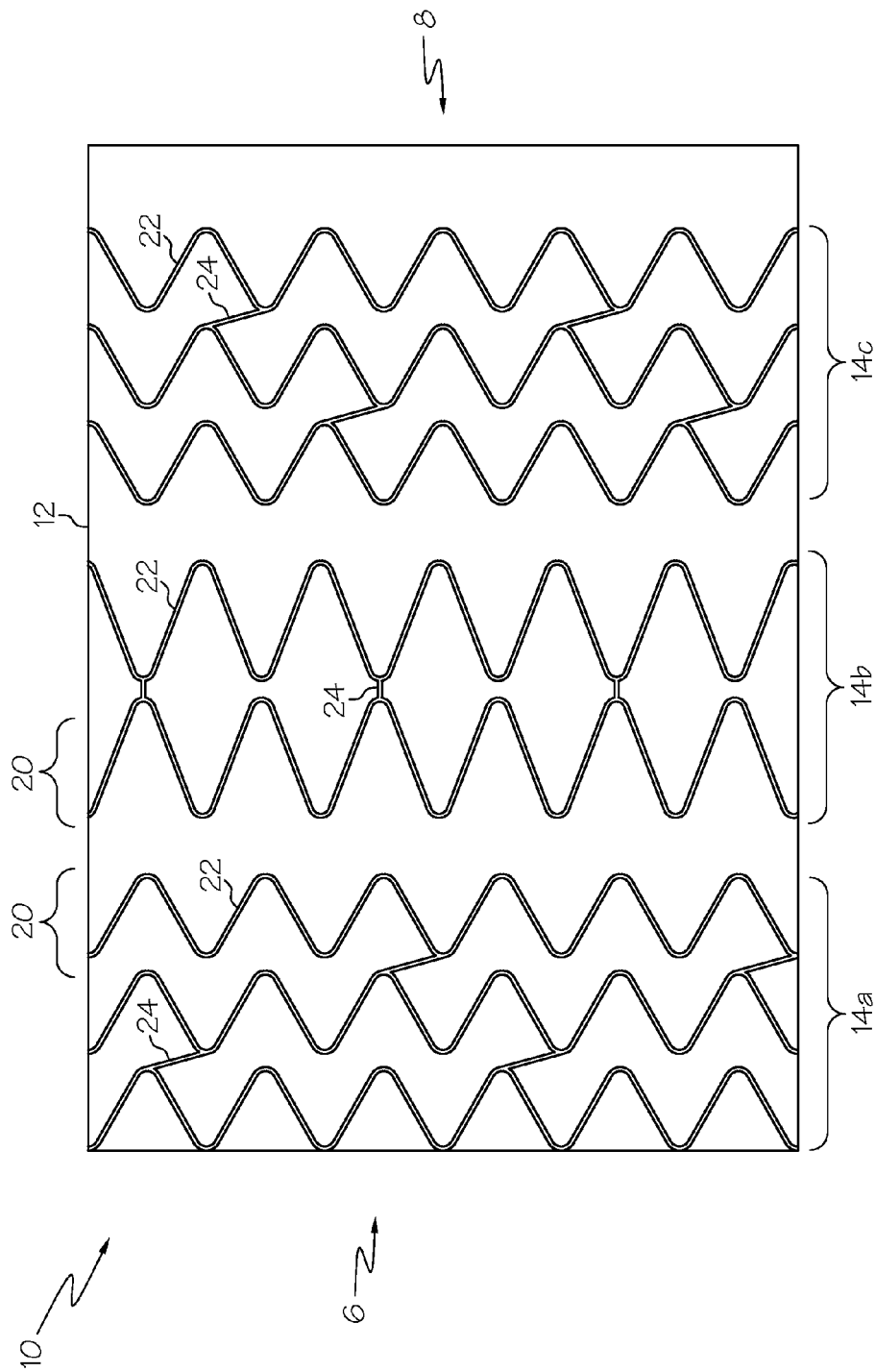
FIG. 2 is a rolled out view of a stent with a tubular body comprising sections of circumferential rings of struts and a bioabsorbable membrane.

FIG. 2 is a stent 10 a tubular wall comprising a bioabsorbable membrane 12 and at least one section 14 comprising at least one circumferential ring 20 of struts 22. In at least one embodiment, the at least one section 14 is embedded within the bioabsorbable membrane 12. Note that the stent 10 design of FIG. 2 is merely an example, it is within the scope of the invention for the stent 10 to have any design so long as it comprises at least two independent sections 14 or "stentlets". Commonly assigned U.S. patent application Ser. No. 11/438,934, entitled Stent with Variable Crimping Diameter, hereby incorporated herein by reference in its entirety, has other non-limiting examples of stent designs comprising at least two independent sections.

The stent 10 in FIG. 2 has three sections 14a,b,c, a first section 14a, a second section 14b and a third section 14c. In a stent 10 comprising only three sections 14a,b,c, the sections 14 can also be referred to as a proximal section 14, a middle section 16, and a distal section 18. It is within the scope of the invention for the stent 10 to have any number of sections 14 or "stentlets". Thus, the stent 10 can have one, two, three, four, five, six, seven, eight, nine, ten or more sections 14. As shown in FIG. 2, the bioabsorbable membrane 12 extends about the entire circumference of the stent 10. In at least one embodiment, the bioabsorbable membrane 12 does not extend about the entire circumference of the stent 10, as discussed in greater detail in reference to FIG. 4.

It is within the scope of the invention for the bioabsorbable membrane 12 to have any longitudinal length between adjacent sections 14. Thus, the longitudinal length of the bioabsorbable membrane 12 between sections 14 can be tailored for the contours of the specific body lumen into which the stent 10 will be placed so that the stentlets 14 are a predetermined distance away from one another in the body lumen. In at least one embodiment, the longitudinal length of the bioabsorbable membrane 12 between adjacent sections 14 is the same. In at least one embodiment, the longitudinal length of the bioabsorbable membrane 12 between adjacent sections 14 is different.

It is within the scope of the invention for each individual section 14 to have one, two, three, four, five, six, seven, eight, nine, ten or more circumferential rings 20 of struts 22 within each section of the stent 10. In at least one embodiment, different sections 14 have different numbers of circumferential rings 20. Adjacent circumferential rings 20 of struts 22 within a section 14 are engaged by at least one connector 24. The connector can be a peak to peak connector, as shown in FIG. 2 or a peak to valley connector.

In at least one embodiment, all three sections 14a,b,c are embedded within a bioabsorbable membrane 12. Note that because the bioabsorbable membrane 12 engages the sections 14a,b,c to one another, there are no members 22,24 that engage the sections 14a,b,c to one another. It is within the scope of the invention for the bioabsorbable membrane 12 to extend beyond the section 18 forming the distal end 8 of the stent 10, as shown in FIG. 2, to extend only as far as the proximal (or distal) ends of the struts 22 of the section 14 forming the end of the stent 10, which, as shown in FIG. 2 is the proximal end 6 of the stent 10 or to extend for the minimum distance needed to engage the sections 14a,b,c and form a tubular stent 10. For example, FIG. 3 has two bioabsorbable membranes 12a,b which instead could be one bioabsorbable membrane 12. This bioabsorbable membrane 12 engages the sections 14a,b,c but does not extend to either the proximal end 6 or the distal end 8 of the stent 10.

Figure 3:
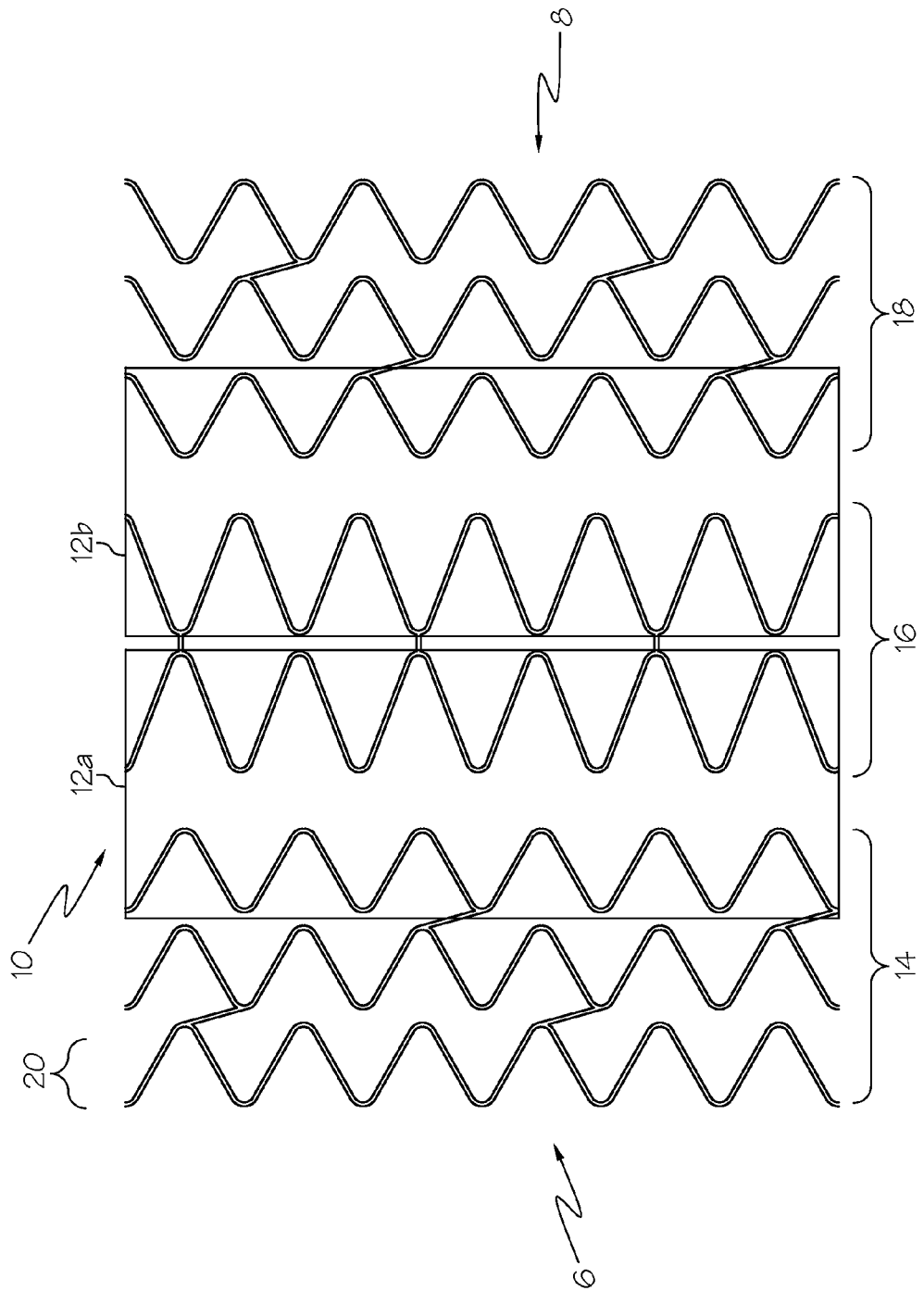
FIG. 3 is a rolled out view of a stent with sections of circumferential rings where the sections of circumferential rings are engaged to each other by two circumferential bioabsorbable membranes.

FIG. 3, is the stent 10 of FIG. 2 with two bioabsorbable membranes 12a,b. As shown in FIG. 3, the distal circumferential ring 20 of the proximal section 14 of the stent 10 and the proximal circumferential ring 20 of the middle section 16 are embedded in the first bioabsorbable membrane 12a. Similarly, the distal circumferential ring 20 of the middle section 16 and the proximal circumferential ring 20 of the distal section 18 are embedded in the second bioabsorbable membrane 12b. It is also within the scope of the invention for the proximal end of the first bioabsorbable membrane 12a to extend to the proximal end 6 of the stent 10 and for the distal end of the second bioabsorbable membrane 12b to extend to the distal end 8 of the stent 10. As shown in FIG. 3, there is a gap between the first bioabsorbable membrane 12a and the second bioabsorbable membrane 12b. The gap can be any length and it is within the scope of the invention for the first and second bioabsorbable membranes 12a,b to be positioned so that the distal edge of the first bioabsorbable membrane 12a abuts the proximal edge of the second bioabsorbable membrane 12b.

In at least one embodiment, the bioabsorbable membrane 12a engaging the proximal section 12 and the middle section 16 is different than the bioabsorbable membrane 12b engaging the middle section 16 and the distal section 18. The bioabsorbable membranes 12a,b can have different chemical compositions or different degradation rates.

Figure 4:
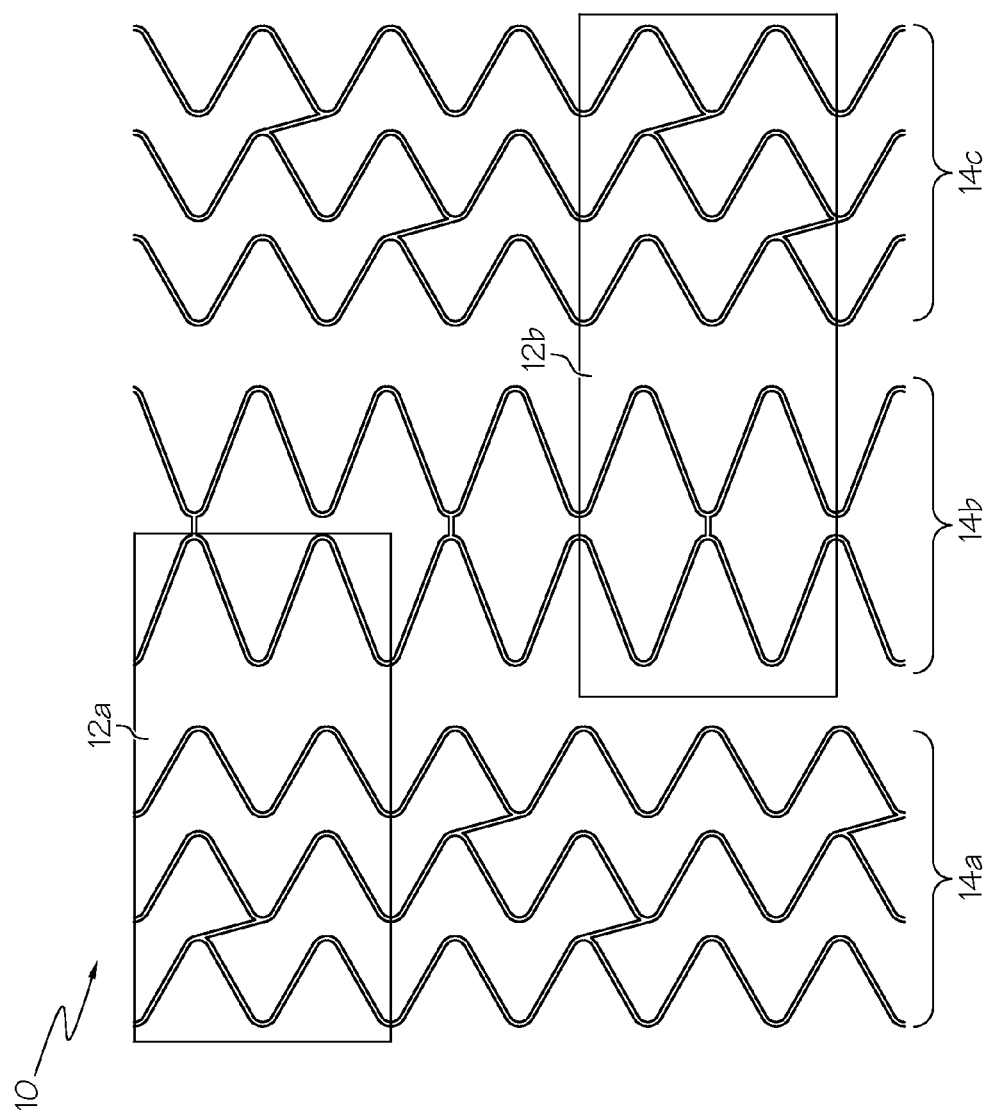
FIG. 4 is a rolled out view of a stent with sections of circumferential rings that are engaged to each other by two longitudinal bioabsorbable membranes that do extend about the entire circumference of the stent

In FIG. 3, each of the two bioabsorbable membranes 12a,b extend about the entire circumference of the stent 10. In at least one embodiment, the stent 10 has at least one bioabsorbable membrane 12 with a circumference that is less than the circumference of the stent 10, as shown in FIG. 4. As shown in FIG. 4, the stent 10 has two bioabsorbable membranes 12a,b with different longitudinal lengths. However, the bioabsorbable membranes can have any longitudinal length.

After the stent 10 is placed within the desired body lumen, the bioabsorbable membrane 12 is absorbed, thereby leaving the individual sections 14a,b,c in place in the body lumen. At this point, the individual sections 14a,b,c act as individual, unconnected stents 14a,b,c. As the above discussion illustrates there are numerous combinations and placements of the bioabsorbable membrane 12 on a particular stent design that results in individual stentlets after the stent 10 has been placed within the body lumen. In at least one embodiment, the stent 10 is placed within the superficial femoral artery.

In at least one embodiment, the stent 10 is positioned within a body lumen so that the bioabsorbable membrane 12 is positioned against a vulnerable plaque. In one embodiment, the bioabsorbable membrane 12 prevents rupturing of the vulnerable plaque during delivery of the stent 10. In this embodiment, the struts 22 of the stent 10 are embedded within the bioabsorable membrane 12 so that the bioabsorbable membrane 12 forms the exterior surface of the stent 10. Note that in this embodiment, any stent design can be used, not just a stent design comprising individual stentlets.

In at least one embodiment, the stent 10 is placed at a bifurcation. In this embodiment, the stent 10 can be positioned so that two sections 14 of the stent 10 are on either side of the ostium of the side branch vessel. Absorption of the bioabsorbable membrane 12 allows blood to flow from the main branch vessel, between the two stenlets 14 on either side of the side branch vessel ostium, into the side branch vessel. This embodiment avoids the problem of stent jailing which occurs when adjacent circumferential rings 20 of struts 22, engaged by connectors 24, impede the flow of blood into the side branch vessel.

Alternatively, the stent 10 can be positioned at the bifurcation and a second balloon catheter is used to punch a hole through the bioabsorbable membrane 12 between the struts 22 and connectors 24 of the stent 10 where the ostium of the side branch vessel meets the stent 10. The second balloon is then inflated to expand the struts 22 and connectors 24 to form a side branch opening in the stent 10, as is known in the art. The bioabsorbable membrane 12 provides stability to the stent 10 during delivery to the bifurcation even though it can be punched through by the second balloon catheter. Blood flows from the main branch vessel through the newly formed side branch opening in the bioabsorbable membrane 12 into the side branch vessel.

Any stent design can be used for this application. If a stent design similar to that of FIG. 2 with individual sections 14 is used then after the bioabsorbable membrane 12 degrades, the stent 10 transforms from one stent to individual stentlets 14. If the stent 10 comprises a plurality of circumferential rings 20 that are engaged to one another by connectors 24, the stent 10 merely loses the bioabsorbable membrane 12. In this case, the use of the second balloon to form a side branch opening prevents stent jailing.

Figure 5:
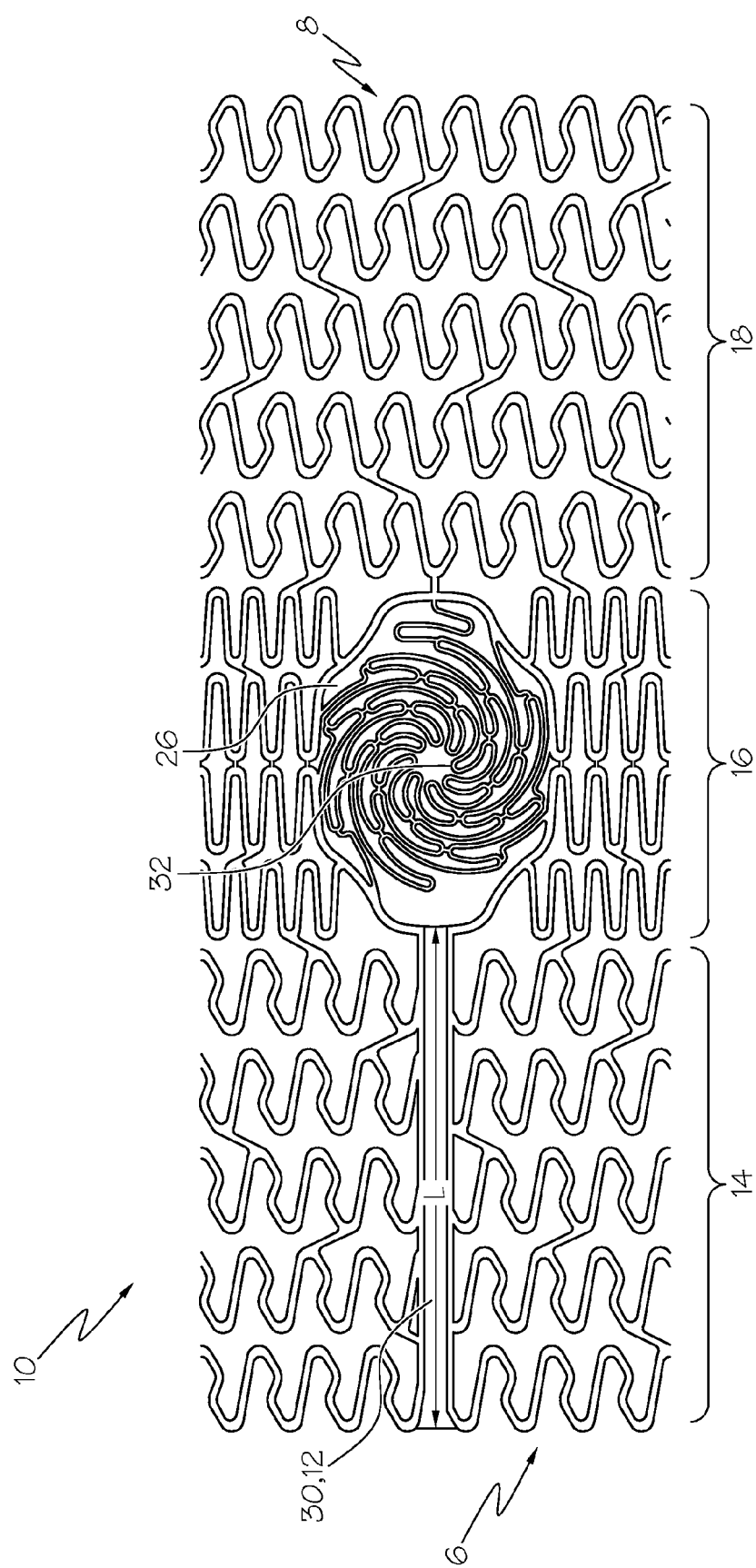
FIG. 5 is a rolled out view of a bifurcated stent with a slit and a bioabsorbable membrane.

FIG. 5 shows a bifurcated stent 10 with a slit 30 and a bioabsorbable membrane 12. Stents with slits and positioning them at a bifurcation, are discussed in greater detail in commonly assigned U.S. application Ser. No. 11/507,103, entitled Alignment Sheath Apparatus and Method, hereby incorporated herein by reference in its entirety. The bifurcated stent 10 has a side branch region comprising at least one side branch member 32 and a side branch opening 26. In this embodiment, the side branch opening 26 is positioned within the middle section 16 of the stent 10. However, the bifurcated stent design in FIG. 5 is a non-limiting example of a bifurcated stent design. The stent 10 can have any design so long as it has a slit 30 extending from the side branch opening to the proximal edge 6 of the stent 10. In some embodiments, the ends of the slit 30 are open and the sides of the slit 30 are defined by a portion of the body of the stent 10. In at least one embodiment, at least a portion of the stent 10 is embedded within the bioabsorbable membrane 12. In one embodiment, the proximal section 14 of the stent 10 is embedded within the bioabsorbable membrane 12. In at least one embodiment, a bioabsorbable membrane 12 is disposed about a bifurcated stent with a slit 30.

In at least one embodiment, the bioabsorbable membrane 12 extends between the sides of the slit 30, along the length of the slit 30. Slit 30 has a longitudinal length (L) that is measured from the proximal edge of the side branch opening 26 to the proximal edge 6 of the stent 10, as shown in FIG. 5. In some embodiments, the longitudinal length of the bioabsorbable membrane 12 equals the longitudinal length (L) of the slit 30, as shown in FIG. 5. However, it is within the scope of the invention for the longitudinal length of the bioabsorbable membrane 12 to be less than the longitudinal length (L) of the slit 30.

In use, the stent 10 is advanced to the desired location within a body lumen. The bioabsorbable membrane 12 covering the slit 30 degrades so that the slit 30 becomes open, thereby preventing entrapment of the alignment guide wire after deployment of the stent 10, as discussed in greater detail in commonly assigned U.S. application Ser. No. 11/507,103.

Figure 6:
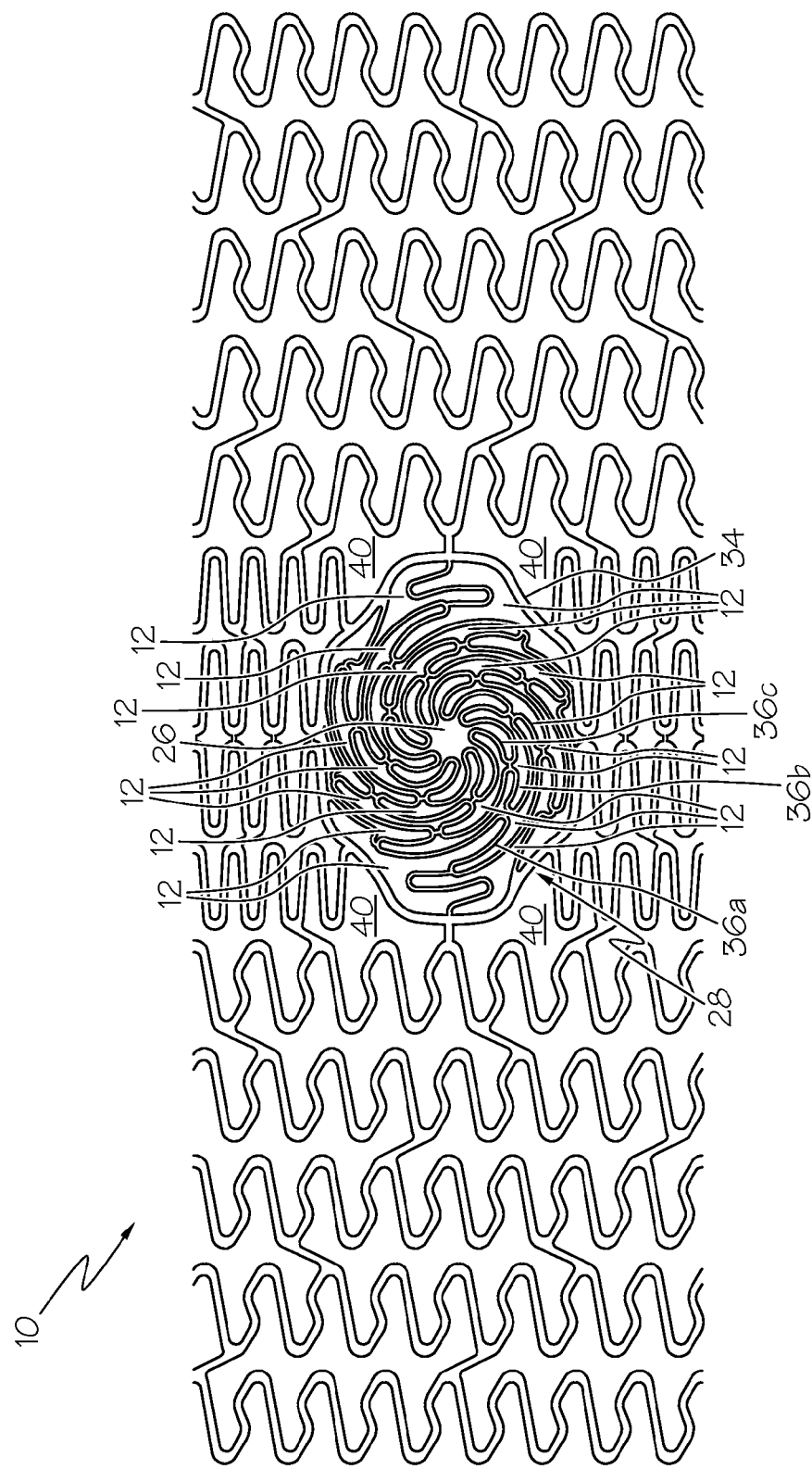
FIG. 6 is a rolled out view of a bifurcated stent with a side branch, where the bioabsorbable membrane forms at least a portion of the side branch.

FIG. 6 is a bifurcated stent 10 with a side branch 28. In this embodiment, the side branch members 32 comprises three concentric rings 36a,b,c and three sets of spiral arms 38a,b,c, however the scope of the invention includes other side branch designs. The embodiment in FIG. 6 also shows a perimeter member 34 that is a separate member from the struts 22 and connectors 24 of the main body of the stent 10. In at least one embodiment, the perimeter member 34 is formed by the struts 22 and connectors 24 of the main body of the stent 10. Other non-limiting examples of side branch designs can be found in commonly assigned U.S. application Ser. No. 11/368,964, entitled Bifurcation Stent with Uniform Side Branch Projection and U.S. application Ser. No. 11/273,186, entitled Stent with Spiral Side-Branch Support Designs, both of which are hereby incorporated herein by reference in their entirety.

Figure 7:
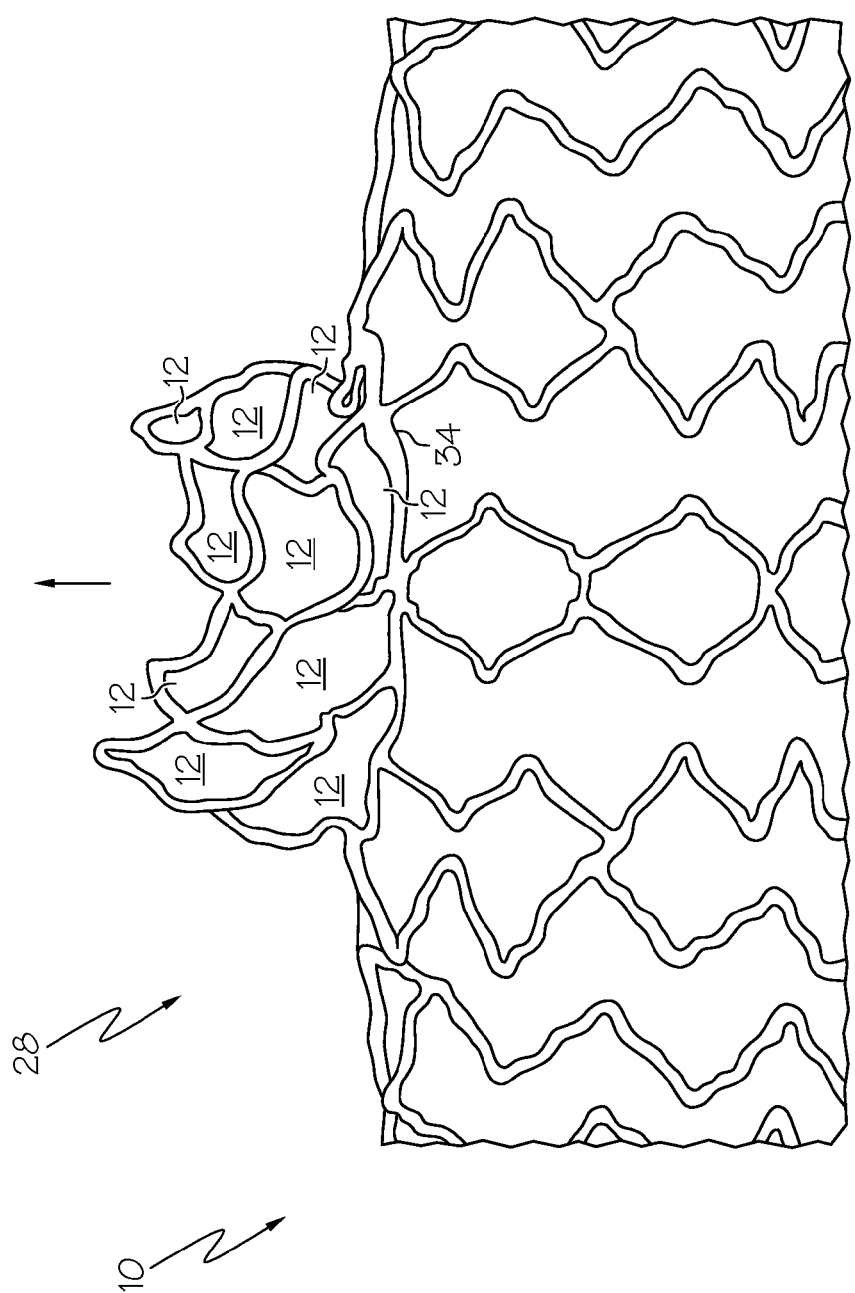
FIG. 7 is a side view of the stent in FIG. 6 in an expanded state.

In at least one embodiment, at least one bioabsorbable membrane 12 spans the spaces or cells between the rings 36 and the spiral arms 38, as shown in FIGS. 6 and 7. In this embodiment, the bioabsorbable membrane 12 forms a portion of the tubular wall of the stent 10 when the stent 10 is in an unexpanded state. If the rings 36 and spiral arms 38 are embedded as shown in FIG. 1a, there will be a plurality of bioabsorbable membranes 12 with one bioabsorbable membrane 12 per cell. If the rings 36 and spiral arms 38 are embedded as shown in either FIG. 1a or 1b, one bioabsorbable membrane 12 can be used to span all the cells. In these embodiments, is also possible to have more than one bioabsorbable membrane 12 that abut one another to provide a contiguous bioabsorbable membrane 12. It is also within the scope of the invention for selected cells to be spanned or covered by a bioabsorbable membrane 12, instead of all the cells as shown in FIGS. 6 and 7. The bioabsorbable membranes 12 can have the same or different chemical compositions and the same or different degradation rates. Thus, one section of the side branch 28 can lose the bioabsorbable membrane 12 before another section of the side branch 28. Similarly, if only selected cells have a bioabsorbable membrane 12, the selected cells can have the same type of bioabsorbable membrane 12 or different types of bioabsorbable membranes 12.

As shown in FIGS. 6 and 7, the area defined by the innermost ring 36 of the side branch 28 does not have a bioabsorbable membrane 12 so that when the bifurcated stent 10 is deployed, blood can flow from the main branch of the stent 10 through the side branch 28 into the side branch vessel, as shown by the arrow in FIG. 7. In at least one embodiment, the bioabsorbable membrane 12 reinforces the side branch members 32, providing additional support. In at least one embodiment, the bioabsorbable membrane 12 increases the coverage of the carina and the rest of the ostium.

Figure 8:
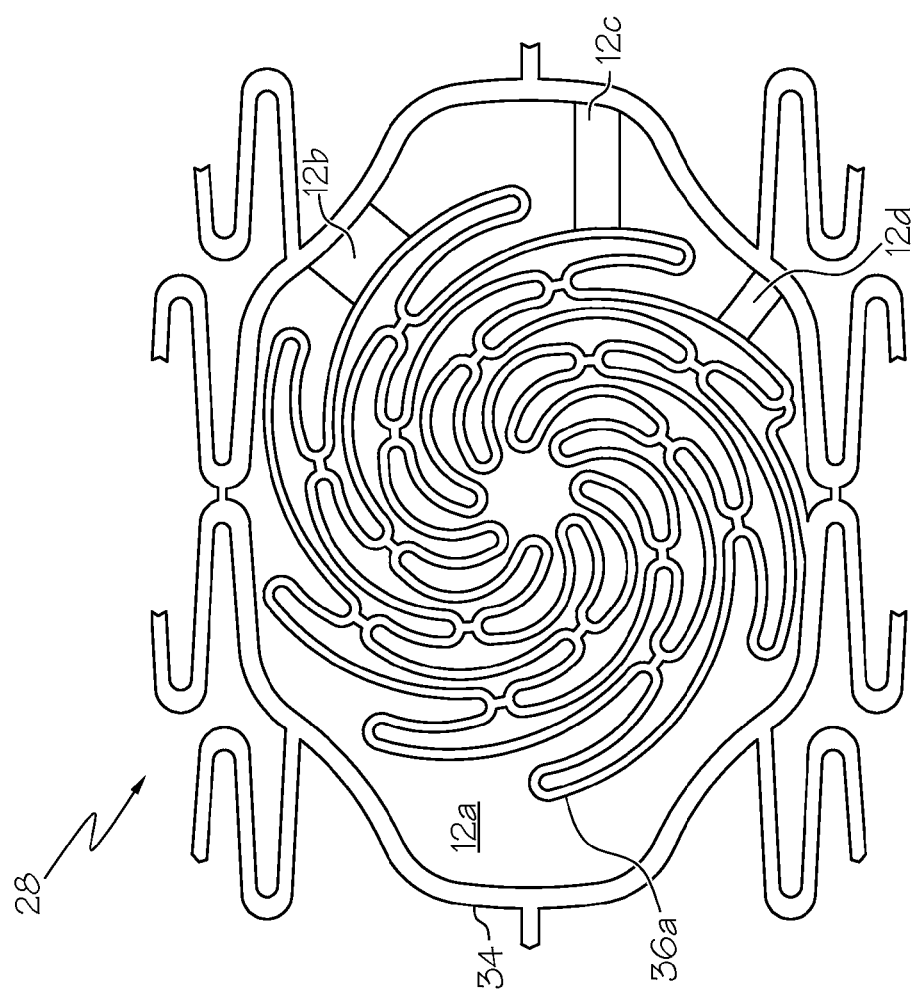
FIG. 8 is an enlarged view of the side branch of the bifurcated stent of FIG. 6 with at least one bioabsorbable membrane engaging the side branch to the perimeter member.
Figure 9:
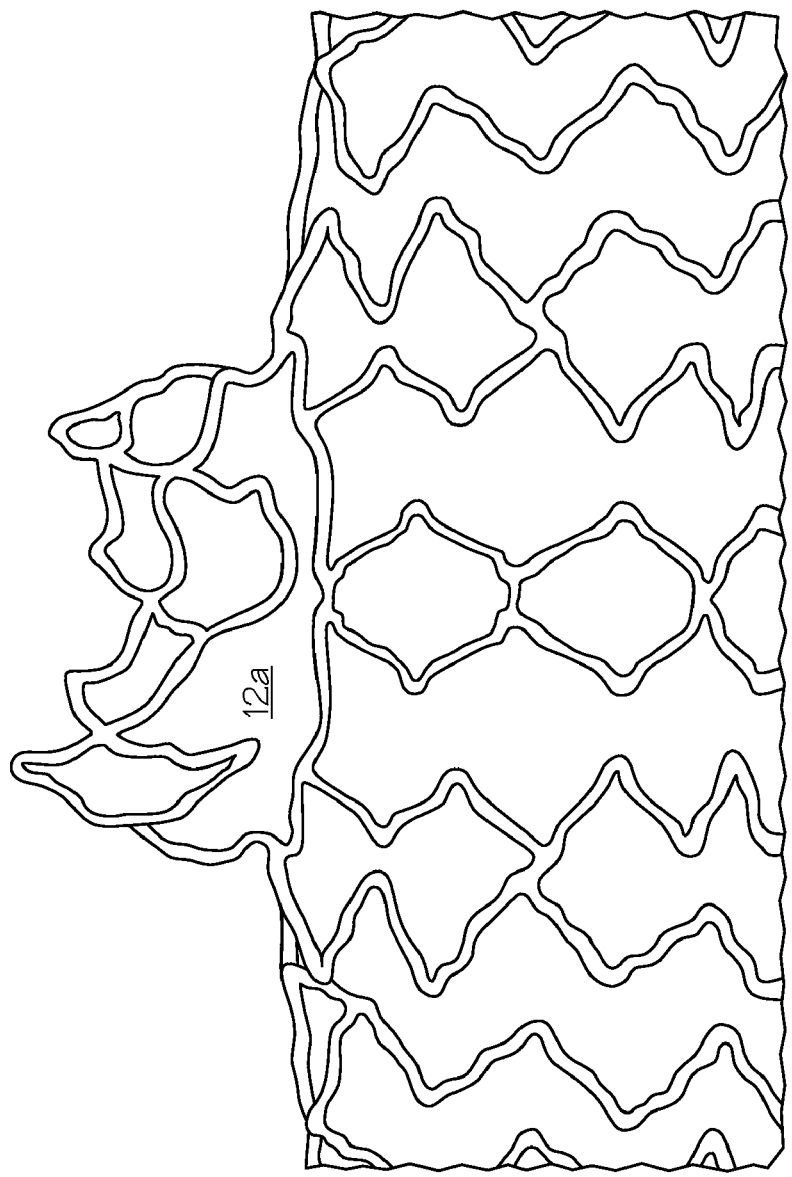
FIG. 9 is the bifurcated stent of FIG. 8 in an expanded state with one bioabsorbable membrane engaging the side branch to the perimeter member.

In at least one embodiment, at least one bioabsorbable membrane 12 engages the side branch 28 and the main body of the bifurcated stent 10, as shown in FIG. 8 which is an enlarged view of the side branch of FIG. 6. In at least one embodiment, one bioabsorbable membrane 12 engages the perimeter member 34 to the first ring 36a, as illustrated in the proximal half of the side branch 28 in FIG. 8. FIG. 9 illustrates this embodiment when the stent 10 is in an expanded state. In this embodiment, when the bioabsorbable membrane 12a degrades, the side branch 28 is a separate stent in the side branch vessel that is not attached to the stent 10 in the main vessel, similar to the stentlets 14 of FIGS. 2-3.

Figure 10:
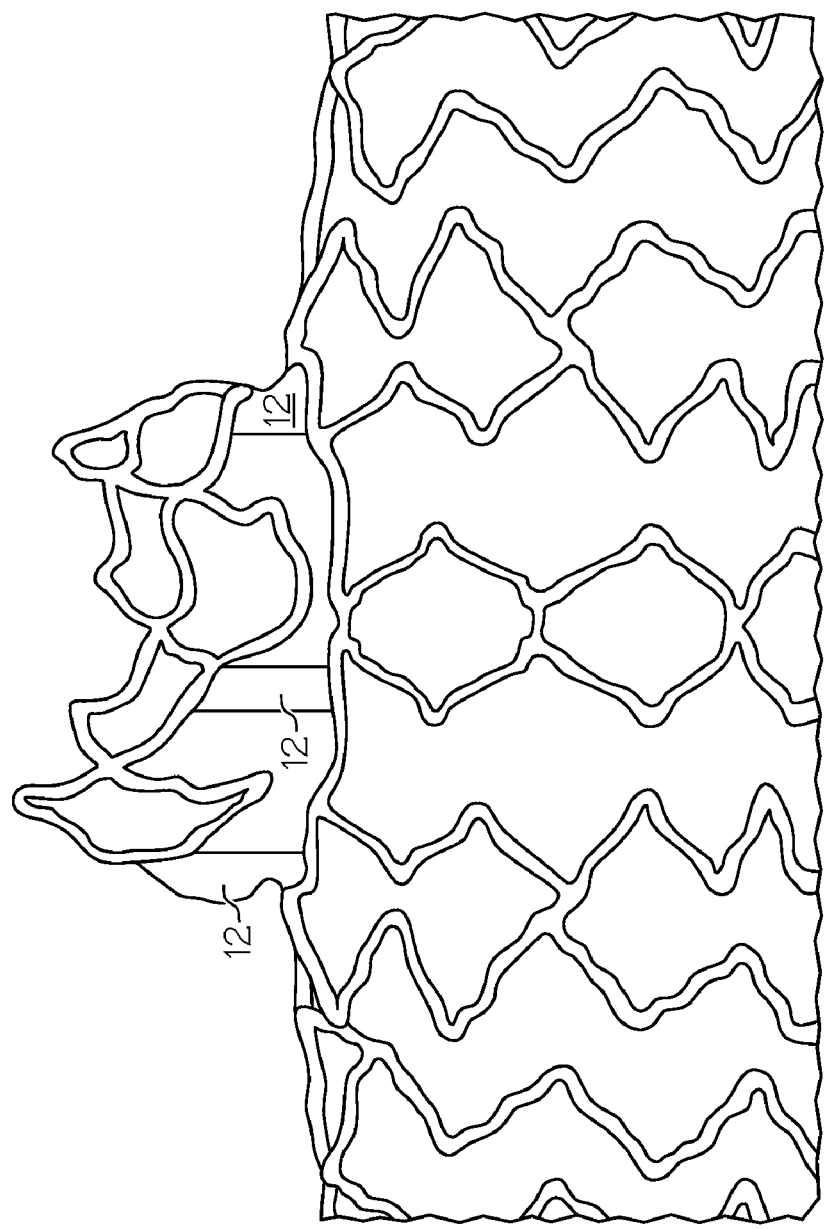
FIG. 10 is the bifurcated stent of FIG. 8 in an expanded state with three bioabsorbable membranes engaging the side branch to the perimeter member.

In at least one embodiment, at least two sections of bioabsorbable membrane 12 engage the perimeter member 34 to the first ring 36a, as illustrated in the distal half of the side branch 28 in FIG. 8. In FIGS. 8 and 10 there are three sections of bioabsorbable membrane 12b,c,d engaging the side branch 28 to the perimeter member 34. It is within the scope of the invention for the sections of bioabsorbable membrane 12 to have any size. These sections of bioabsorbable membrane 12 can be thought of as linking the side branch 28 and the perimeter member 34. As discussed above, the sections of bioabsorbable membrane 12 can have the same or different chemical compositions and the same or different degradation rates.

In at least one embodiment, at least one bioabsorbable membrane 12 covers selected cells in the region of the bifurcation. These selected cells can be a part of the side branch 28, as discussed above, in reference to FIGS. 6-9 or these selected cells can be adjacent to the side branch 28. For example, cells 40 in FIG. 6 can be spanned by at least one bioabsorbable membrane 12. In at least one embodiment, all cells adjacent to the side branch 28 are spanned by at least one bioabsorbable membrane 12. Note that not all cells in the region of the bifurcation are labeled. In at least one embodiment, bioabsorbable membranes 12 link the side branch 28 and the perimeter member 34 as well as spanning selected cells adjacent to the side branch 28. In at least one embodiment, the bioabsorbable membrane(s) 12 spanning cells adjacent to the side branch 28 provide additional coverage to the carina and the rest of the ostium. In at least one embodiment, the bioabsorbable membrane 12 reinforces the side branch 28, providing additional support to the side branch 28.

Figure 11:
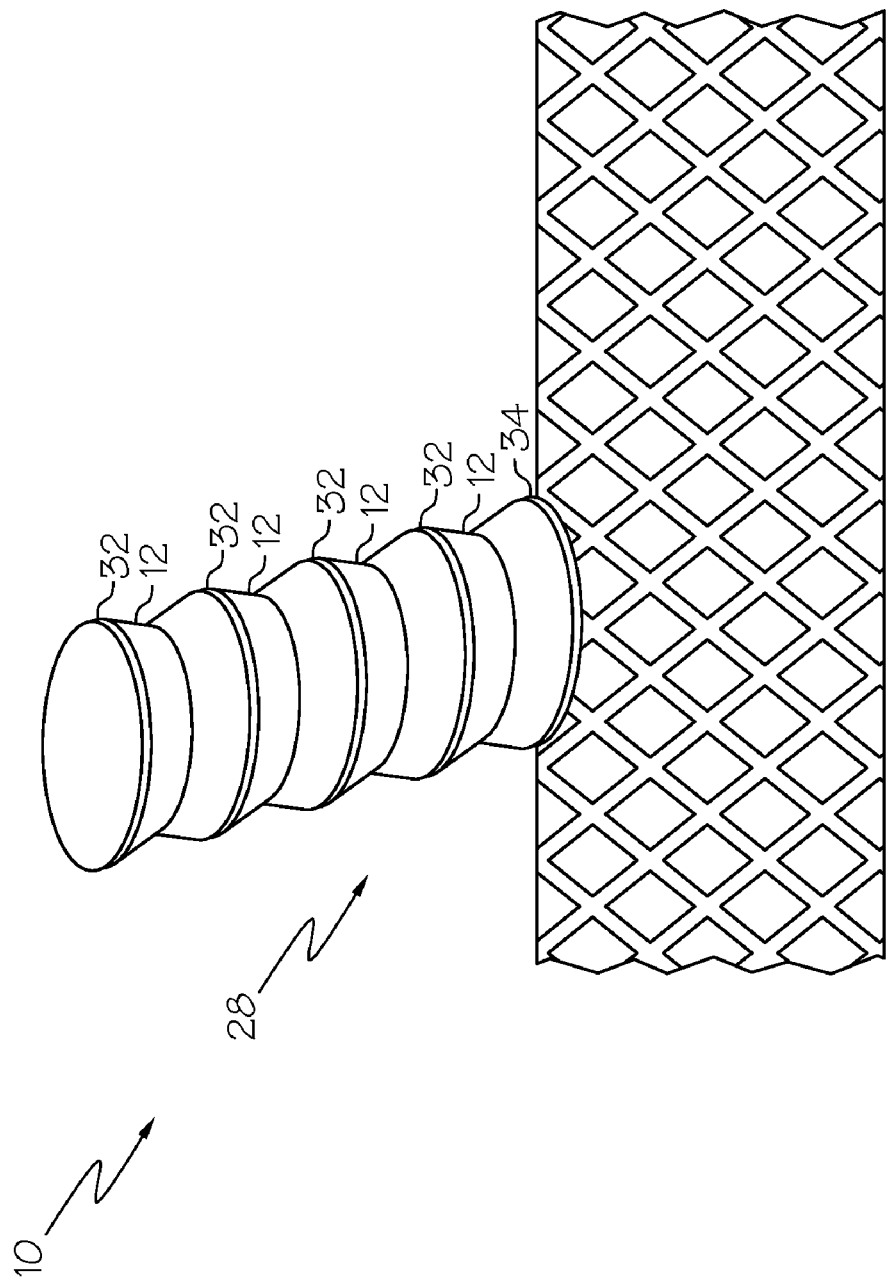
FIG. 11 is a side view of a bifurcated stent with a telescoping side branch comprising four rings and four bioabsorbable membranes in an expanded state.
Figure 12:
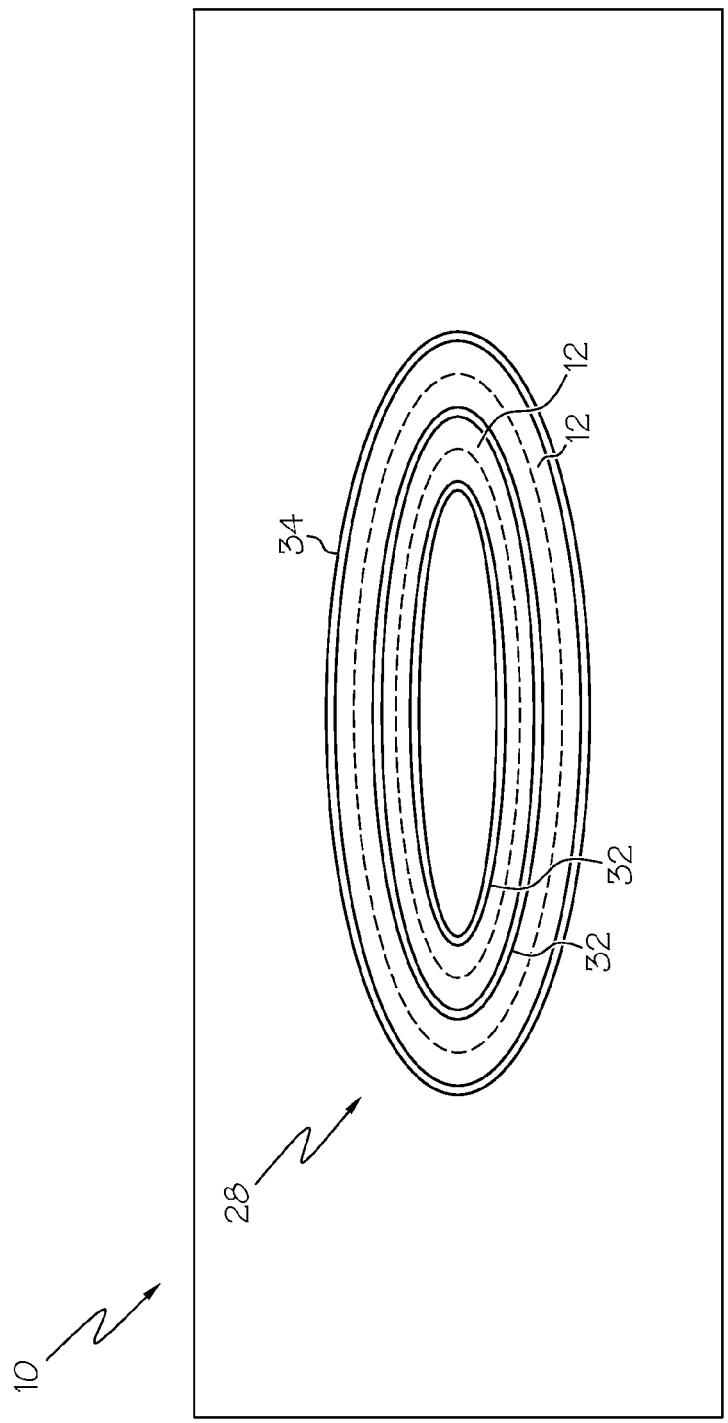
FIG. 12 is a rolled out view of a stent with a telescoping side branch comprising two rings and two bioabsorbable membranes.

FIGS. 11 and 12 illustrate a bifurcated stent 10 with a telescoping side branch 28 in a rolled out view and in an expanded view. Telescoping bifurcated stents are discussed in greater detail in commonly assigned U.S. patent application Ser. No. 11/300,210, entitled Telescoping Bifurcated Stents, hereby incorporated herein by reference in its entirety. Note that the main body of the bifurcated stent 10 can have any configuration, so the main body of the stent 10 in FIG. 12 does not have any structure.

The side branch 28 comprises at least one side branch member 32. In FIG. 11, the side branch 28 has four side branch members 32, each of which in the form of a ring. It is within the scope of the invention for the side branch 28 to have one, two, three, four, five, six, seven, eight, nine, ten or more rings 32. The rings 32 can have any width, thickness, circumferential length and shape. In at least one embodiment, the rings 32 can have sequentially decreasing circumferences to form a tapered side branch 28.

The side branch members 32 are engaged to one another and to the perimeter member 34 of the side branch 28 by at least one bioabsorbable membrane 12. In at least one embodiment, the bioabsorbable membrane 12 is pleated, or folded between rings 32, as shown in FIGS. 11 and 12. In FIG. 12, the pleating is indicated by dashed lines. Folding or pleating the bioabsorbable membrane 12 between rings 32 increases the distance between the rings 32 when the side branch 28 is in an expanded state. The bioabsorbable membrane 12 can have any number of pleats or folds. When the side branch 28 is in an unexpanded state, the side branch 28 forms a part of the tubular wall of the stent 10. Thus, the bioabsorbable membranes 12 form a part of the tubular wall of the stent 10.

As discussed above, the side branch 28 has at least one bioabsorbable membrane 12. In at least one embodiment, the bioabsorbable membrane 12 engaging the side branch 28 to the perimeter member 34 is different from the at least one bioabsorbable membrane 12 engaging the rings 32 to one another. As discussed previously, bioabsorbable membranes 12 can have different chemical compositions and/or different degradation rates. In at least one embodiment, Each of the stent embodiments discussed above can be configured to deliver at least one therapeutic agent. In at least one embodiment, the portions of the stent 10 that are not embedded within the bioabsorbable membrane 12 elute therapeutic agents. In at least one embodiment, the portions of the stent 10 embedded within the bioabsorbable membrane 12 elute therapeutic agents. In one embodiment, the therapeutic agent is not eluted from the stent 10 until the delivery mechanism, e.g. a coating retainer, is exposed due to the degradation of the bioabsorbable membrane 12. In another embodiment, therapeutic agent is eluted from the portions of the stent 10 embedded within the bioabsorbable membrane 12 before the bioabsorbable membrane 12 degrades. In this embodiment, the members (struts 22 and/or connectors 24) of the stent 10 are embedded in the ways illustrated in the cross-sections of FIG. 1a or 1c. In both of those embodiments, there is at least one surface of the member (struts 22 and/or connectors 24) from which therapeutic agent can be eluted. Mechanisms to deliver therapeutic regimens of therapeutic agents and examples of therapeutic agents are discussed in greater detail in commonly assigned U.S. Pat. No. 7,135,039, entitled Intraluminar Perforated Radially Expandable Drug Delivery Prosthesis and A Method For the Production Thereof, and U.S. Pat. No. 6,783,543, entitled Intravascular Stent With Increasing Coating Retaining Capacity, both of which are hereby incorporated herein by reference in its entirety.

Bioabsorbable membranes may also be used to form a portion of the catheter used to deliver a stent. Catheter assemblies used to deliver a stent at a bifurcation often have a side branch guide wire which is used to orient the bifurcated stent at the bifurcation. A side branch guide wire housing houses the side branch guide wire. The side branch guide wire housing is positioned between the catheter and the stent and in at least one embodiment, extends through the side branch opening of the stent. The side branch guide wire housing may be separate from the catheter or engaged to the catheter. Catheters with a side branch guide wire lumen are discussed in greater detail in commonly assigned U.S. Patent Application Publication 2004/0172121, entitled Rotating Balloon Expandable Sheath Bifurcation Delivery and U.S. Patent Application Publication 2003/0181923, entitled Methods for Deploying Stents in Bifurcations, both of which are hereby incorporated herein by reference in its entirety. As shown in these two publications, catheter assemblies of this type can have many different configurations.

Figure 13:
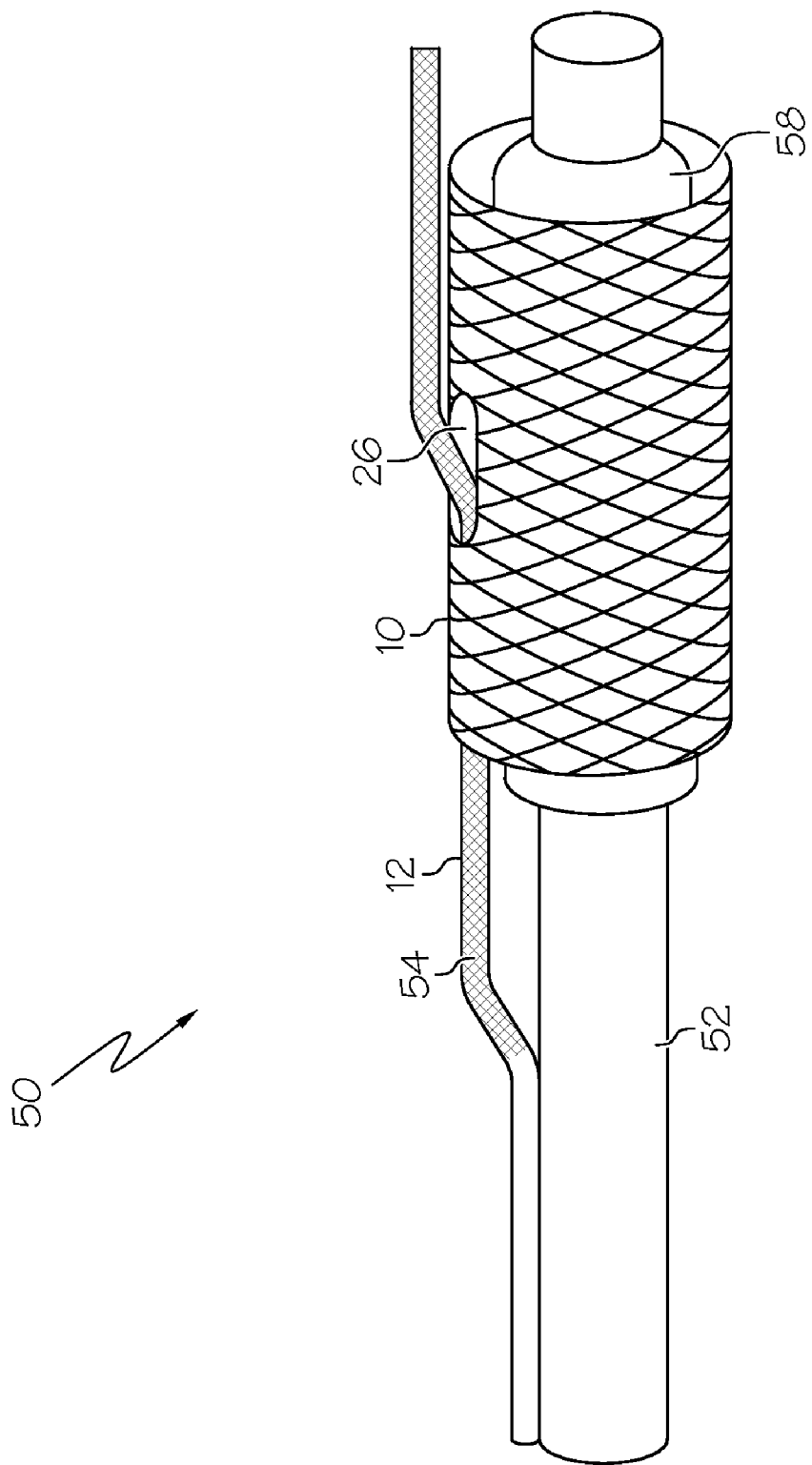
FIG. 13 is a side view of a stent delivery system with a bioabsorbable membrane forming the distal end region of the side branch guide wire housing.
Figure 14:
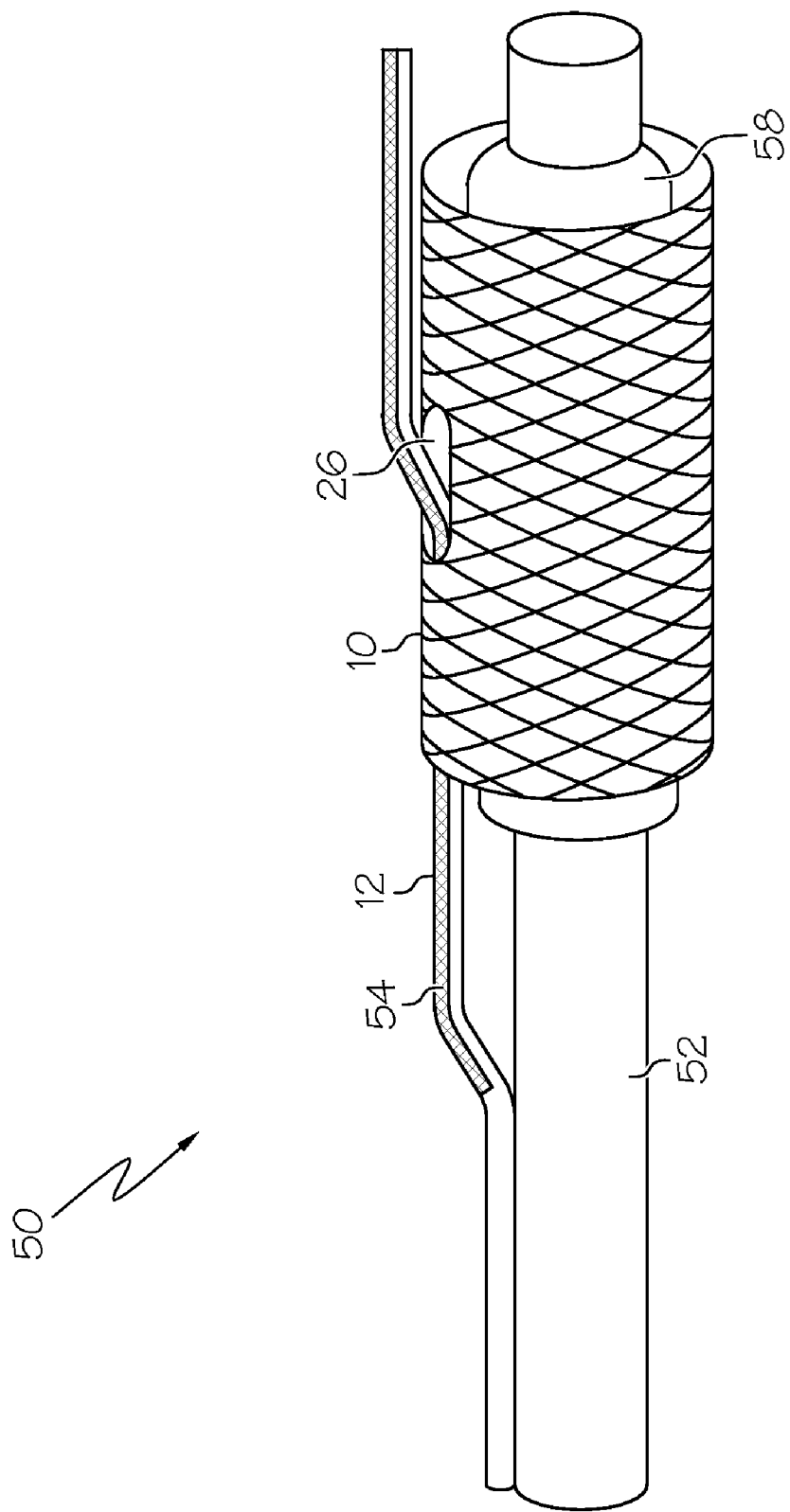
FIG. 14 is a side view of a stent delivery system with a bioabsorbable membrane forming a portion of the circumference of the distal end region of the side branch guide wire housing.

In at least one embodiment, a bioabsorbable membrane forms at least a portion of the side branch guide wire housing. In one embodiment, a bioabsorbable membrane forms the distal end region of the side branch guide wire housing. FIG. 13 is a non-limiting example of a catheter assembly 50 with a bifurcated stent 10 and a side branch guide wire housing 54 between the stent 10 and the catheter 52. As shown in FIG. 13, a bioabsorbable membrane 12 forms the distal end region of the side branch guide wire housing 54 and is indicated by cross-hatching. In another embodiment, a bioabsorbable membrane 12 forms a portion of the circumference of the distal end region of the side branch guide wire housing 54. In this embodiment, the bioabsorbable membrane 12 can be thought to form a strip extending along the length of the distal end region of the side branch guide wire housing 54. In one embodiment, the strip of bioabsorbable membrane 12 forms the portion of the side branch guide wire housing 54 that is adjacent to the interior surface of the stent 10 being deployed by the catheter assembly 50, as shown in FIG. 14 by cross-hatching.

In use, a bifurcated stent 10 is positioned at a bifurcation with the catheter assembly 50. The portion of the side branch guide wire housing 54 made of bioabsorbable membrane 12 is absorbed. In at least one embodiment, absorption of the bioabsorbable membrane 12 aids the withdrawal of the catheter assembly 50.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof.

Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising a substantially cylindrical tubular body, the tubular body defining a primary lumen, the tubular body comprising a wall and at least one perimeter member defining at least one opening in the wall, the tubular body having at least one expandable side branch, the at least one expandable side branch having an expanded state, in the expanded state the at least one expandable side branch defining a secondary lumen, the primary lumen in fluid communication with the secondary lumen via the at least one opening in the wall, the at least one side branch comprising a plurality side branch members, the plurality of side branch members being engaged to the at least one perimeter member, and at least a portion of the tubular body being embedded in at least one bioabsorbable membrane, the at least one perimeter member comprising a first perimeter member, the plurality of side branch members comprising a first ring, the at least one bioabsorbable membrane comprising a first bioabsorbable membrane,
the first bioabsorbable membrane engaging the first ring and the first perimeter member, and
the first bio absorbable membrane having at least one fold.

2. The stent of claim 1, the plurality of side branch members further comprising a second ring, the second ring being engaged to the first ring by a second bioabsorbable membrane.

3. The stent of claim 2, the second bioabsorbable membrane having at least one fold.

4. The stent of claim 2, the first bioabsorbable membrane having a different degradation rate than the second bioabsorbable membrane.

5. A stent, the stent comprising a substantially cylindrical tubular body, the tubular body defining a primary lumen, the tubular body comprising a wall and at least one perimeter member defining at least one opening in the wall, the tubular body having at least one expandable side branch, the at least one expandable side branch having an expanded state, in the expanded state the at least one expandable side branch defining a secondary lumen, the primary lumen in fluid communication with the secondary lumen via the at least one opening in the wall, the at least one side branch comprising a plurality side branch members, the plurality of side branch members being engaged to the at least one perimeter member, and at least a portion of the tubular body being embedded in at least one bioabsorbable membrane, the at least one perimeter member further defining a slit region, the slit region having a proximal end and a distal end, the proximal end of the slit region being the proximal end of the substantially cylindrical tubular body, the distal end of the slit region being the at least one opening in the wall, the slit region having a first side and a second side, the at least one bioabsorbable membrane extending between the first and second sides of the slit region thereby forming a portion of the tubular body, the at least one bioabsorbable membrane having a length at most equal to the distance between the proximal end of the slit region to the at least one opening in the wall.

6. A method for making a stent for a bifurcation, comprising:
providing a stent, the stent comprising a plurality of circumferential rings of struts, adjacent circumferential rings of struts being engaged by a plurality of connectors, the plurality of circumferential rings and the plurality of connectors being embedded in a bioabsorbable membrane;
placing the stent at a bifurcation of a main branch vessel and a side branch vessel;
expanding the stent;
creating an opening in the bioabsorbable membrane after the stent has been placed at the bifurcation, the opening aligned with the bifurcation so that blood flows from the main branch vessel into the side branch vessel.

7. A stent, the stent comprising a substantially cylindrical tubular body, the tubular body defining a primary lumen, the tubular body comprising a wall and at least one perimeter member defining at least one opening in the wall, the tubular body having at least one expandable side branch, the at least one expandable side branch having an expanded state, in the expanded state the at least one expandable side branch defining a secondary lumen, the primary lumen in fluid communication with the secondary lumen via the at least one opening in the wall, the at least one side branch comprising a plurality side branch members, the plurality of side branch members being engaged to the at least one perimeter member, and at least a portion of the tubular body being embedded in at least one bioabsorbable membrane, the at least one perimeter member comprising a first perimeter member, the plurality of side branch members comprising a first ring and a second ring,
the at least one bioabsorbable membrane comprising a first bioabsorbable membrane and a second bioabsorbable membrane, the second bioabsorbable membrane having at least one fold, the second ring being engaged to the first ring by the second bioabsorbable membrane.

8. The stent of claim 7, the first ring being engaged to the first perimeter member by the first bio absorbable membrane.

9. The stent of claim 7, the first bioabsorbable membrane having a different degradation rate than the second bioabsorbable membrane.

* * * * *